US007819830B2

(12) United States Patent
Sindel et al.

(10) Patent No.: US 7,819,830 B2
(45) Date of Patent: Oct. 26, 2010

(54) KNEE BRACE WITH MECHANICAL ADVANTAGE CLOSURE SYSTEM

(75) Inventors: Chad M. Sindel, Pleasant Hill, CA (US); Craig J. Koloske, Tracy, CA (US); John M. Petlansky, Tracy, CA (US)

(73) Assignee: Top Shelf Manufacturing, Inc., Tracy, CA (US)

( * ) Notice: Subject to any disclaimer, the term of this patent is extended or adjusted under 35 U.S.C. 154(b) by 262 days.

(21) Appl. No.: 11/511,307

(22) Filed: Aug. 29, 2006

(65) Prior Publication Data

US 2007/0060853 A1 Mar. 15, 2007

Related U.S. Application Data

(60) Provisional application No. 60/712,173, filed on Aug. 30, 2005.

(51) Int. Cl.

| | |
|---|---|
| ***A61F 5/00*** | (2006.01) |
| ***A61F 5/58*** | (2006.01) |
| ***A61F 5/37*** | (2006.01) |
| ***A61M 21/00*** | (2006.01) |

(52) U.S. Cl. ............................ 602/16; 602/23; 602/26; 128/882

(58) Field of Classification Search .................. 602/16, 602/26, 61, 62, 36, 38, 40, 27, 30, 4, 5, 28, 602/29, 19, 20, 23, 60, 65; 62/63; 128/882
See application file for complete search history.

(56) References Cited

U.S. PATENT DOCUMENTS

| | | | | |
|---|---|---|---|---|
| 4,100,918 | A * | 7/1978 | Glancy | 602/16 |
| 4,370,978 | A * | 2/1983 | Palumbo | 602/26 |
| 4,863,471 | A * | 9/1989 | Mansat | 623/13.2 |
| 5,613,943 | A * | 3/1997 | Palumbo | 602/62 |
| 6,110,138 | A * | 8/2000 | Shirley | 602/26 |
| 6,551,264 | B1 * | 4/2003 | Cawley et al. | 602/16 |
| 7,118,543 | B2 | 10/2006 | Telles et al. | |
| 7,306,571 | B2 * | 12/2007 | Schwenn et al. | 602/12 |
| 2003/0100855 | A1 * | 5/2003 | Norstrem | 602/27 |
| 2007/0073207 | A1 | 3/2007 | Sindel et al. | |

* cited by examiner

*Primary Examiner*—Patricia M Bianco
*Assistant Examiner*—Ophelia Hawthorne
(74) *Attorney, Agent, or Firm*—Dickstein Shapiro LLP

(57) ABSTRACT

An orthopedic knee orthosis having a closure unit with a pull system that provides a mechanical advantage for applying user-desired forces to the knee joint structures and yet permits the knee joint to move within a range of motion during activity by the user. A method of using the orthopedic knee orthosis by placing the orthosis over a user's knee, wrapping the orthosis around the user's knee, and tightening the orthosis to apply user-defined forces to the knee joint structures.

13 Claims, 2 Drawing Sheets

KNEE BRACE WITH MECHANICAL ADVANTAGE CLOSURE SYSTEM

RELATED APPLICATION

This patent application claims priority to U.S. Provisional Application, No. 60/712,173, filed on Aug. 30, 2005, the entire disclosure of which is incorporated by reference herein.

BACKGROUND OF THE INVENTION

1. Field of the Invention

The present invention is directed to a closure system for a knee brace with an improved pull system to provide a mechanical advantage for applying compression forces to the knee.

2. Description of the Related Art

Knee braces are commonly worn by patients for treatment of an injury to the knee joint. Knee braces stabilize the joint to control its lateral movement, while they limit joint flexion and/or extension in an adjustable and controllable manner to prevent recurrence of injury to the knee.

Various designs for knee braces are known in the art. A well-known design employs adjustable support members, according to which medial and/or lateral support pads are positioned adjacent to the medial and lateral sides of the knee joint to provide comfort and support to the user by stabilizing the knee joint against lateral movement. However, lateral support by the pads require an adjustable screw design to laterally adjust the position of the pad relative the knee joint. This design necessitates using a tool to rotatably adjust the screw members, which requires that the tool be readily available to the user when readjustment of the setting of the pad assembly is needed.

While many of the current knee brace designs provide a degree of support to the knee joint, there is a need to provide an improved knee brace which allows for simple and effective adjustment of the brace. A knee brace which offers greater positive support to the knee joint structures and yet permits the knee joint to move within the normal range of motion during activity by the user is also needed. There is also a demand for an economical knee brace that can be conveniently used by a patient for a mechanical advantage in exerting compression on the knee.

SUMMARY OF THE INVENTION

The present invention provides a closure unit for an orthopedic knee brace that utilizes a closure mechanism comprising two separate pieces working together to create a mechanical advantage ("compression-action") to complete the necessary function of the brace. The mechanical advantage is achieved as the two separate pieces work together through the force enacted from a single pull handle. Preferably, the system may be affixed to a brace formed of soft neoprene, nylon, or foam material, to anatomically fit around the knee. The knee brace of the present invention may be used in the treatment of patella subluxations and dislocations, chronic and acute mal-tracking of patella, and patellofemoral pain and dysfunctions, for example.

The closure unit is disposed on the brace and includes a first connector member having a series of channels, and a second connector member. An elongated flexible pull member is operatively weaved around the series of channels to provide a mechanical force advantage when tightened by the patient to draw the first connect member and the second connect member against the patient's knee to exert compression forces.

The elongated flexible pull member can comprise a cord such as a polyester cord with an exterior braided configuration. The cord is connected at its distal end to a strap handle, which can receive a nap or hook material that can be appropriately positioned, for example, on the lateral side of the knee brace, so that a patient who pulls the cord to tighten the knee brace can then secure it at a desired compression.

BRIEF DESCRIPTION OF THE DRAWINGS

Other features and advantages of the present invention will become apparent when the following detailed description is read in conjunction with the accompanying drawings, in which.

DETAILED DESCRIPTION OF THE PREFERRED EMBODIMENT

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein to specifically provide an knee orthosis with an improved pull system to apply compression forces.

Figure 1:
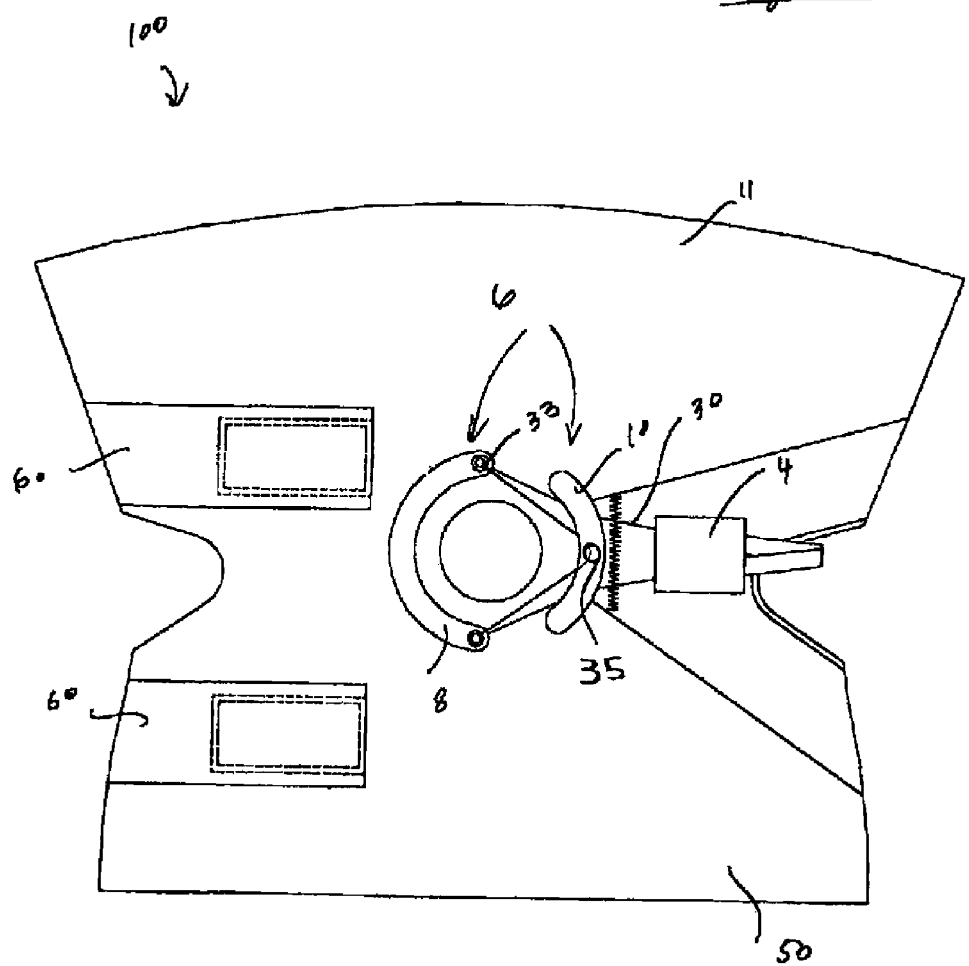
FIG. 1 is a front layout view of the knee brace of the present invention.
Figure 2:
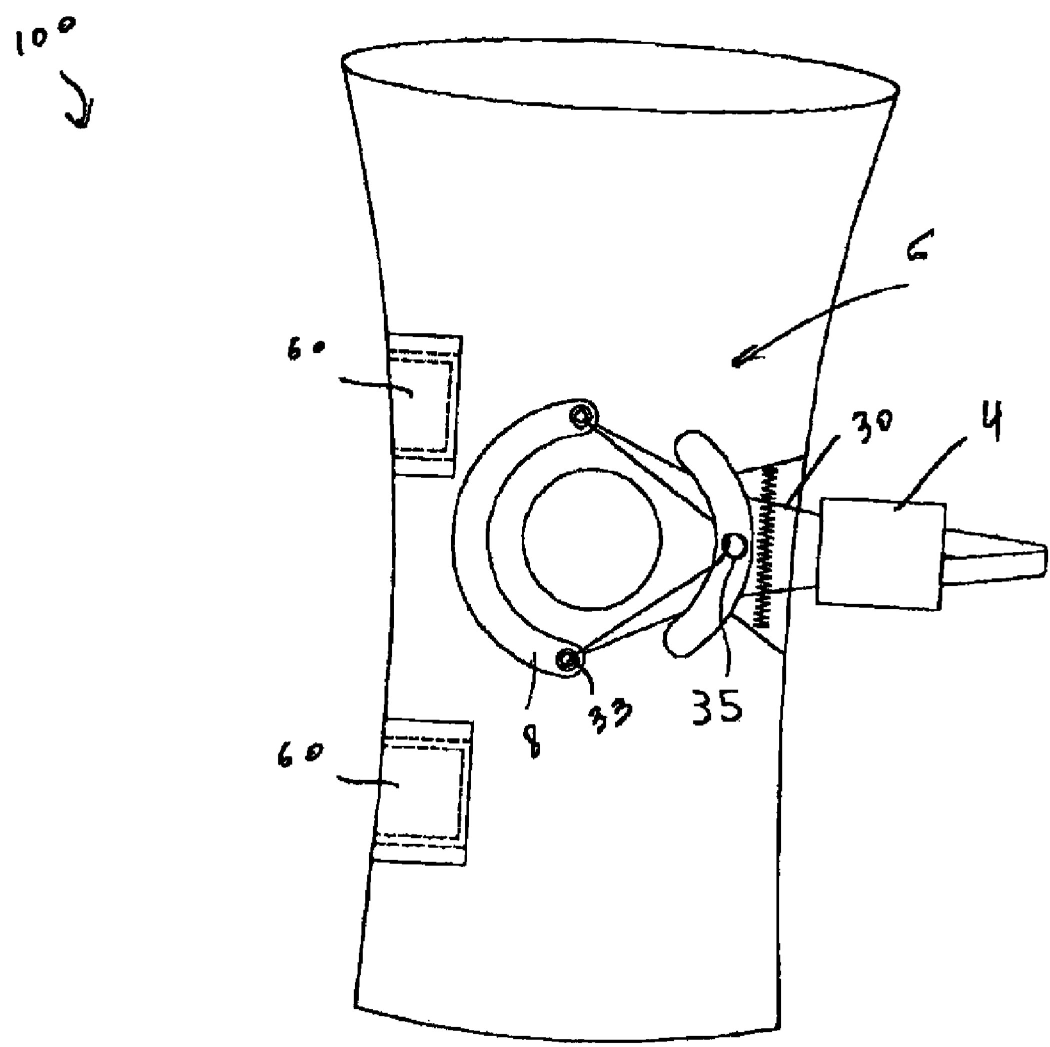
FIG. 2 is a view of the knee brace of the present invention as it would appear when wrapped around a patient's knee.

FIGS. 1 and 2 illustrate an exemplary embodiment of knee brace or orthosis 100 which permits a patient to provide compressive forces about his/her knee by simply pulling and removably fastening a fastener member 4 to a surface portion of the orthosis.

As can be seen in FIG. 1, a closure unit 6 is provided on side 11 of the orthosis 100. Closure unit 6 includes a first connector member 8 and a second connector member 10. In an exemplary embodiment, the first connector member 8 and the second connector member 10 are provided on body member 50 that wraps around and conforms to the shape of a patient's knee. Body member 50 may comprise neoprene, nylon or foam material, for example, to anatomically fit around the knee.

The orthosis may be provided with separate straps or attaching members 60, as shown in FIGS. 1 and 2. The straps 60 may be, for example, hook and loop fasteners (e.g., Velcro™ brand straps) attached to body member 50 to allow engagement of the orthosis 100 and to further secure member 50 to the patient's knee. The straps can be appropriately secured in position by securing the free ends of the straps to the orthosis 100.

Referring to FIG. 1, and in accordance with an exemplary embodiment of the present invention, the closure unit 6 includes a C-shaped first connector member 8. In a preferred embodiment, connector member 8 is provided with channels 33. Although FIG. 1 illustrates only two channels 33 through connector member 8, it must be understood that the invention contemplates a closure unit having any number of channels on the connector member.

Also illustrated in FIG. 1 is an elongated flexible member or cord 30, which can be formed from a polyester material having an exterior braided surface to thereby provide a low friction, but strong, pull member. The cord member 30 slides within a single pivot channel 35 in second connector member 10 and in channels 33 in first connector member 8 to thereby reduce the friction of a normal brace, while also providing a mechanical advantage or force multiplier when the cord 30 is pulled by the patient.

The cord 30 is connected at its end to a strap handle 4. The user, by pulling upon the strap, can then employ a mechanical advantage, via cord 30 and the channels 33 to pull the respective first connector member 8 and second connector member 10 together to provide a compressive force on the knee. The strap can then be appropriately secured in position by securing the free end of the strap to the orthosis.

The ability of the cord 30 to slide with low friction within the channels 33 provides a relatively compact efficient mechanical advantage without requiring additional moving parts such as pulleys or posts. Thus, a relatively economical and compact adjustable knee orthosis with an improved closure unit is provided.

The above description and drawings illustrate preferred embodiments which achieve the objects, features and advantages of the present invention. It is not intended that the present invention be limited to the illustrated embodiments, but rather only by the appended claims.

What is claimed as new and desired to be protected by Letters Patent of the United States is:

1. An orthopedic knee orthosis, comprising:

a body member comprising an opening to receive a knee; and a closure unit mounted on the body member, said closure unit further comprising:

a first connector member conforming to the shape of the knee, a second connector member; and a single flexible pull member having a first end and a second end and which passes through a first channel of the first connector, then through a pivot channel of the second connector, then through a second channel of the first connector;

wherein the first end and second end of the pull member are connected to a same strap handle, such that, when tension is applied to the flexible pull member via the strap handle, the body member is tightened by action of a mechanical advantage between the first connector member and the second connector member, wherein the first connector member has at least one more channels than the second connector member, and wherein the channels of the first connector member and the at least one pivot channel of the second connector member are positioned such that the flexible pull member does not substantially overlap the body member opening.

2. The orthopedic knee orthosis of claim 1, wherein said flexible pull member is operatively weaved through the channels of said first connector member and the pivot channel of said second connector member.

3. The orthopedic knee orthosis of claim 2, wherein said strap handle receives a fastening means to hold said flexible pull member in a tightened position determinable by a wearer.

4. The orthopedic knee orthosis of claim 3, wherein said fastening means comprises a hook and loop material.

5. The orthopedic knee orthosis of claim 1, further comprising an attaching member for securing the orthosis in a tightened position.

6. The orthopedic knee orthosis of claim 5, wherein attaching member comprises a hook and loop strap.

7. The orthopedic knee orthosis of claim 1, wherein said body member further comprises at least one of neoprene, nylon, and foam.

8. The orthopedic knee orthosis of claim 1, wherein said flexible pull member comprises a cord.

9. The orthopedic knee orthosis of claim 1, wherein said flexible pull member is made of a material comprising polyester and having a braided configuration.

10. The orthopedic knee orthosis of claim 1, wherein the channels of the first and second connectors are eyelets.

11. The orthopedic knee orthosis of claim 1, further comprising a handle coupled to ends of the flexible pull member.

12. The orthopedic knee orthosis of claim 1, wherein said body member further comprises at least one attaching member for securing the body member to the knee.

13. A method of using an orthopedic knee orthosis for treatment of a patella, comprising:

placing an orthopedic knee orthosis over a patient's knee, wherein said orthopedic knee orthosis comprises:

a body member conforming to the shape of a patient's knee comprising an opening to receive the knee; and a closure unit mounted on the body member, said closure unit further comprising:

a first connector member conforming to the shape of the knee;

a second connector member and a flexible pull member which passes through a first channel of the first connector, then through a pivot channel of the second connector, then through a second channel of the first connector, wherein the first connector member has at least one more channels than the second connector member, and wherein the channels of the first connector member and the at least one pivot channel of the second connector member are positioned such that such that the flexible pull member does not substantially overlap the body member opening; wrapping said body member around said patient's knee; tightening the orthosis by pulling on the flexible pull member, and securing said orthosis in a tightened position.

* * * * *